United States Patent
Anderson et al.

(10) Patent No.: US 9,956,378 B2
(45) Date of Patent: *May 1, 2018

(54) CATHETER ASSEMBLY

(71) Applicant: CathRx Ltd, Homebush Bay (AU)

(72) Inventors: Neil Lawrence Anderson, Roseville (AU); Evan Ka-Loke Chong, South Strathfield (AU); David Ogle, Cowan (AU); James Panos, Earlwood (AU)

(73) Assignee: CathRx Ltd., Homebush Bay (AU)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/804,269

(22) Filed: Jul. 20, 2015

(65) Prior Publication Data

US 2015/0320974 A1 Nov. 12, 2015

Related U.S. Application Data

(63) Continuation of application No. 13/125,033, filed as application No. PCT/AU2009/001421 on Oct. 30, 2009, now Pat. No. 9,084,869.

(Continued)

(51) Int. Cl.
*A61M 25/00* (2006.01)
*A61B 5/04* (2006.01)
(Continued)

(52) U.S. Cl.
CPC .... *A61M 25/0043* (2013.01); *A61M 25/0041* (2013.01); *A61M 25/0152* (2013.01);
(Continued)

(58) Field of Classification Search
CPC ....... A61N 1/04; A61M 25/04; A61M 25/005; A61M 25/0147; A61M 29/02;
(Continued)

(56) References Cited

U.S. PATENT DOCUMENTS 5,100,423 A 3/1992 Fearnot et al.
5,228,442 A 7/1993 Imran
(Continued)

FOREIGN PATENT DOCUMENTS

WO 2002032497 A1 4/2002
WO 2002045608 A2 6/2002
(Continued)

OTHER PUBLICATIONS

Search Report for PCT/AU2009/001421, dated Dec. 23, 2009, 5 pages.

(Continued)

*Primary Examiner* — Scott Medway
(74) *Attorney, Agent, or Firm* — TraskBritt

(57) ABSTRACT

A catheter assembly comprises a first elongate tubular member having a proximal end portion defining a proximal end, a distal end portion having an opening therein and defining a distal end, and at least one lumen defined between the proximal end and the distal end. A second elongate tubular member has a proximal end portion defining a proximal end, a distal end portion defining a distal end, and at least one lumen defined between the proximal end and the distal end. The second elongate tubular member is received within the at least one lumen of the first elongate tubular member, such that the distal end portion of the second elongate tubular member projects from the opening in the distal end portion of the first elongate tubular member. An elongate, shape-imparting element is receivable in the at least one lumen of at least one of the first elongate tubular member and the second elongate tubular member. The shape-imparting element imparts a non-rectilinear shape to the distal end portion of at least one of the first elongate tubular member and the second elongate tubular member.

19 Claims, 9 Drawing Sheets

Related U.S. Application Data

(60) Provisional application No. 61/110,522, filed on Oct. 31, 2008.

(51) Int. Cl.
*A61B 18/14* (2006.01)
*A61M 25/01* (2006.01)

(52) U.S. Cl.
CPC ............. *A61B 5/04* (2013.01); *A61B 18/1492* (2013.01); *A61M 25/0147* (2013.01); *A61M 2025/0004* (2013.01); *A61M 2025/0161* (2013.01); *A61M 2025/0163* (2013.01); *A61M 2210/125* (2013.01)

(58) Field of Classification Search
CPC ... A61F 9/00745; A61B 5/0422; A61B 19/22; A61B 18/24; A61B 18/1206; A61B 18/1492
See application file for complete search history.

(56) References Cited

U.S. PATENT DOCUMENTS

| | | | |
|---|---|---|---|
| 5,282,845 A | | 2/1994 | Bush et al. |
| 5,456,667 A | | 10/1995 | Ham et al. |
| 5,486,161 A | | 1/1996 | Lax et al. |
| 5,527,279 A | | 6/1996 | Imran |
| 5,549,109 A | | 8/1996 | Samson et al. |
| 5,582,609 A | | 12/1996 | Swanson et al. |
| 5,617,854 A | * | 4/1997 | Munsif .......................... 600/374 |
| 5,730,741 A | | 3/1998 | Horzewski et al. |
| 5,741,249 A | | 4/1998 | Moss et al. |
| 5,836,947 A | | 11/1998 | Fleischman et al. |
| 5,938,694 A | | 8/1999 | Jaraczewski et al. |
| 5,972,019 A | | 10/1999 | Engelson et al. |
| 6,004,319 A | | 12/1999 | Goble et al. |
| 6,090,104 A | | 7/2000 | Webster, Jr. |
| 6,096,036 A | | 8/2000 | Bowe et al. |
| 6,241,665 B1 | | 6/2001 | Negus et al. |
| 6,325,797 B1 | * | 12/2001 | Stewart et al. .................. 606/41 |
| 6,352,531 B1 | * | 3/2002 | O'Connor .......... A61B 1/00071 385/43 |
| 6,391,018 B1 | | 5/2002 | Tanaka et al. |
| 6,592,581 B2 | | 7/2003 | Bowe |
| 6,711,444 B2 | | 3/2004 | Koblish |
| 6,771,996 B2 | | 8/2004 | Bowe et al. |
| 6,966,908 B2 | | 11/2005 | Maguire et al. |
| 7,039,450 B2 | | 5/2006 | Duarte |
| 7,081,115 B2 | | 7/2006 | Taimisto |
| 7,435,248 B2 | | 10/2008 | Taimisto et al. |
| 7,781,040 B2 | | 8/2010 | Coyle |
| 7,815,762 B2 | | 10/2010 | Lentz et al. |
| 7,935,108 B2 | | 5/2011 | Baxter et al. |
| 8,062,284 B2 | | 11/2011 | Booth |
| 8,187,264 B2 | | 5/2012 | Kobayashi |
| 8,260,394 B2 | | 9/2012 | Anderson et al. |
| 8,798,706 B2 | | 8/2014 | Kim et al. |
| 2002/0004644 A1 | | 1/2002 | Koblish |
| 2004/0039371 A1 | | 2/2004 | Tockman et al. |
| 2005/0222557 A1 | * | 10/2005 | Baxter et al. .................. 606/16 |
| 2008/0015409 A1 | | 1/2008 | Barlow et al. |
| 2008/0233318 A1 | | 9/2008 | Coyle |
| 2008/0249525 A1 | | 10/2008 | Lee et al. |

FOREIGN PATENT DOCUMENTS

| | | |
|---|---|---|
| WO | 2003094764 A1 | 5/2003 |
| WO | 2004028233 A2 | 4/2004 |
| WO | 2004100813 A3 | 1/2005 |
| WO | 2005070491 A3 | 9/2005 |
| WO | 2006135988 A1 | 12/2006 |

OTHER PUBLICATIONS

Written Opinion for PCT/AU2009/001421, dated Dec. 23, 2009.
European Office Action and Supplementary European Search Report for EP 09822903.2, dated Mar. 5, 2012, 7 pages.
Japanese Office Action for JP Application No. P2011-533487, dated Sep. 24, 2013, 4 pages.
International Preliminary Report on Patentability for International Application No. PCT/AU2009/001421, dated May 2, 2011, 10 pages.
Australian Examination Report for Australian Application No. 2009310635, dated Jan. 9, 2015, 4 pages.

* cited by examiner

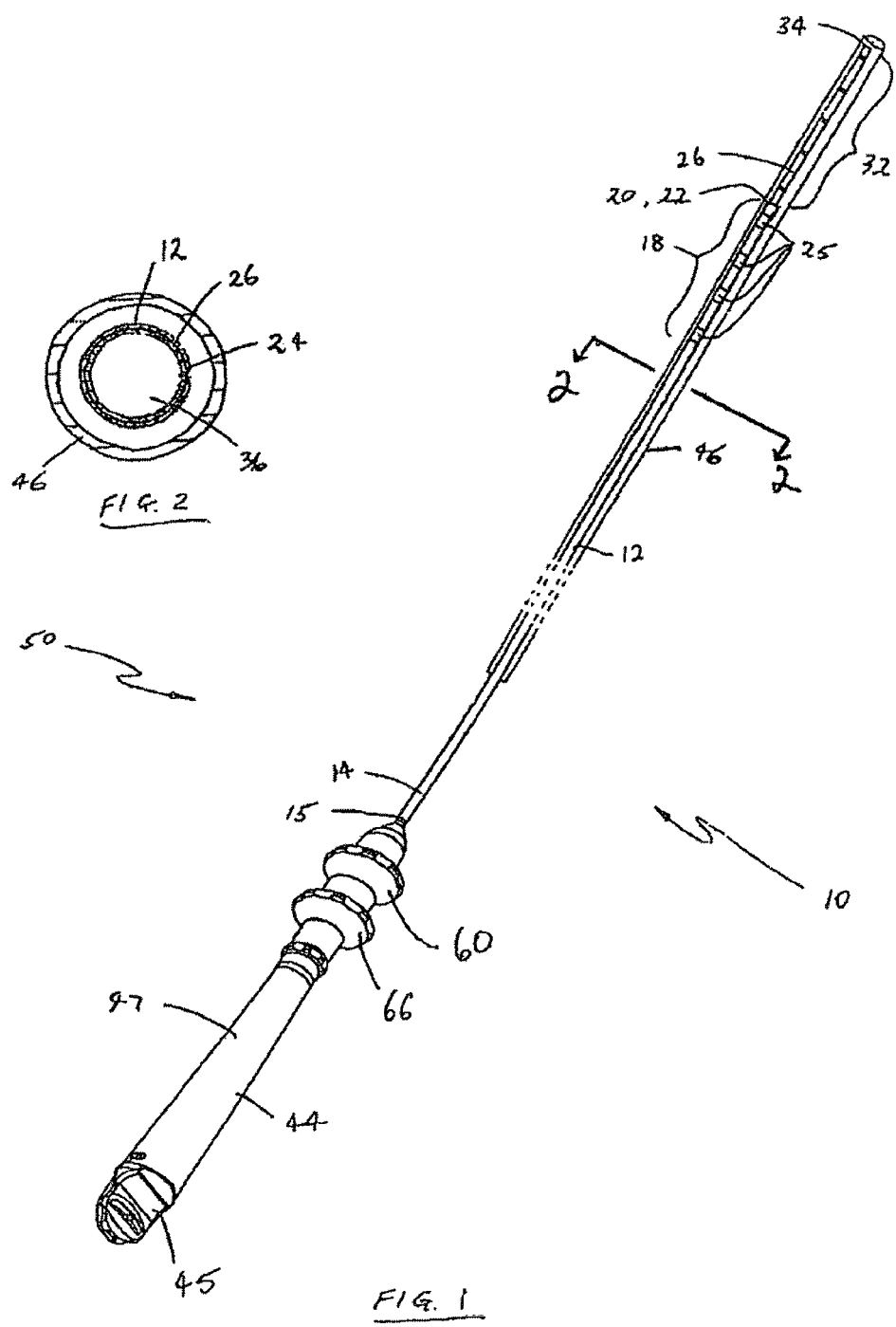

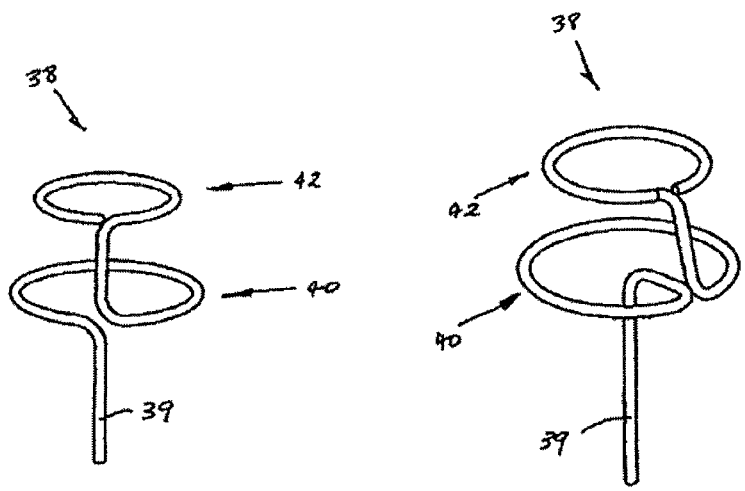
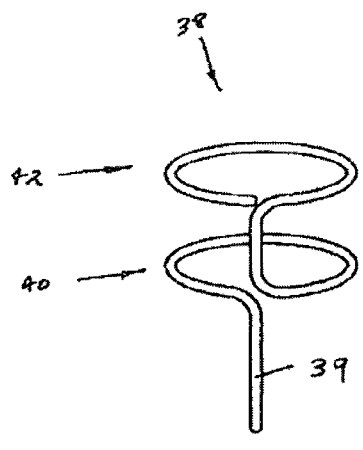

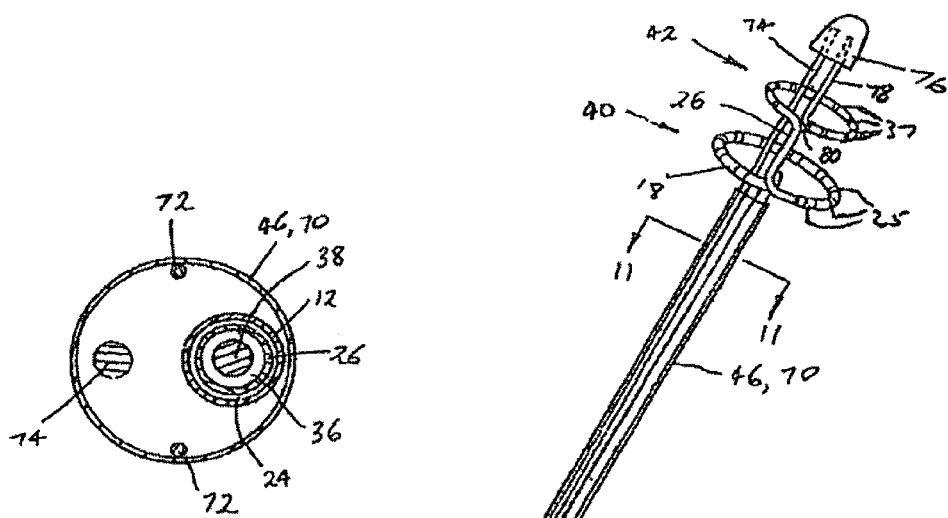
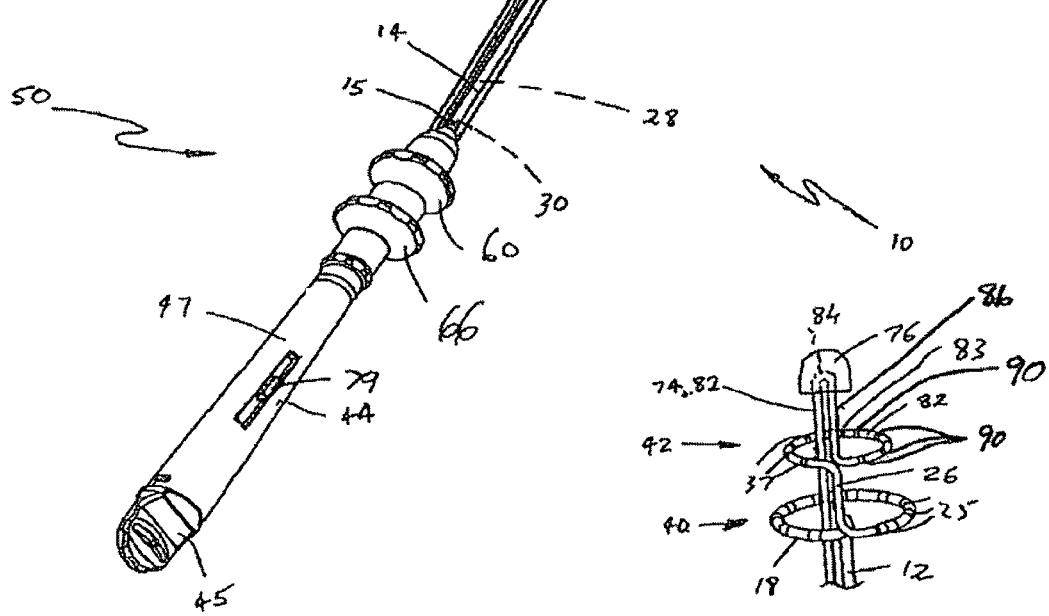
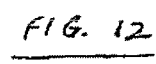

CATHETER ASSEMBLY

CROSS-REFERENCE TO RELATED APPLICATIONS

This application is a continuation of U.S. patent application Ser. No. 13/125,033, filed Apr. 19, 2011, now U.S. Pat. No. 9,084,869, issued Jul. 21, 2015, which is a national phase entry under 35 U.S.C. § 371 of International Patent Application PCT/AU2009/001421, filed Oct. 30, 2009, published in English as International Patent Publication WO 2010/048676 A1 on May 6, 2010, which claims the benefit under Article 8 of the Patent Cooperation Treaty to U.S. Provisional Patent Application Ser. No. 61/110,522 filed Oct. 31, 2008, the disclosures of each of which are incorporated herein by reference in their entirety.

TECHNICAL FIELD

The present disclosure relates, generally, to a catheter assembly and, more particularly, to a catheter assembly having a first catheter tube and a second catheter tube that are both able to be introduced into an anatomical site through a single introduction path.

The catheter assembly has been developed primarily for use in diagnosing and/or treating heart conditions, particularly heart arrhythmias. However, it will be appreciated that the catheter assembly is not limited to this particular use and may also be used to diagnose or treat other conditions.

BACKGROUND

Catheter systems are becoming an increasingly common way of diagnosing and treating abnormal heart conditions, in particular, heart arrhythmias. Such arrhythmias can be treated with drugs or by use of electronic devices such as pacemakers. However, these treatments alleviate, rather than cure, the condition.

In contrast, the use of ablative techniques has been shown to cure arrhythmias. Thus, catheters having mapping electrodes and/or ablative electrodes are inserted through the vascular system of a patient's body so that a distal end of the catheter can be placed accurately in the relevant chamber of the heart. For the treatment of atrial fibrillation, the distal end is placed at or around the ostium of one or more of the pulmonary veins, in turn, to effect ablation.

In still other applications of ablative catheters, the catheter may be placed against a wall of a blood vessel or organ, for example, for heating tumors to treat such tumors. It is, therefore, desirable that a distal end of the catheter be substantially planar so that the distal end of the catheter assembly can be placed in contact with the wall of the vessel or organ.

A catheter assembly is disclosed in U.S. Pat. No. 6,771,996 ("the '996 patent"). This catheter assembly includes an outer catheter having a lumen and an inner catheter sized to fit within and slide through the lumen of the outer catheter. Both catheters may be introduced into an anatomical site through a single introduction path. At the distal end region of each catheter is an electrode system. One electrode system is for mapping the site; the other is for ablating the site. The distal end regions of the catheters are able to assume a predetermined coiled or radially expanded configuration in the absence of an external force. During introduction of the inner and outer catheters into the anatomical site, a guide wire extends through the catheters to deform the catheters from their naturally coiled or expanded configuration into a constrained linear configuration. Alternatively, a cylindrical introducer is placed over the catheters to constrain the catheters. Once the distal ends of the catheters have been placed at the desired anatomical location, the guide wire or introducer is removed to allow the catheters to assume their predetermined coiled or radially expanded configurations.

A disadvantage of each of the catheter system embodiments disclosed in the '996 patent is that the inner and outer catheters assume a specific, predetermined configuration after insertion. Accordingly, the shape of the catheters cannot be adjusted after insertion to account for differences in anatomical geometries. Therefore, a large variety of differently configured catheters must be provided to cater for these differing geometries. Moreover, the time taken to complete a procedure on a patient can be significantly increased if the initially inserted catheter system needs to be swapped with a differently configured catheter system during the procedure. This additional time means that the patient, and in some cases the physician, has longer exposure to radiation or drugs required during the procedure.

A further disadvantage of the catheter system embodiments disclosed in the '996 patent is that the inner catheter extends through an opening in the sidewall of the outer catheter. It can be difficult to align the distal end of the inner catheter with the sidewall opening in the outer catheter. The sidewall opening also complicates manufacture of the outer catheter and represents a location of potential weakness in the outer catheter.

BRIEF SUMMARY OF THE INVENTION

In a first aspect, there is provided a catheter assembly that comprises:
 a first elongate tubular member having a proximal end portion defining a proximal end, a distal end portion having an opening therein and defining a distal end, and at least one lumen defined between the proximal end and the distal end;
 a second elongate tubular member having a proximal end portion defining a proximal end, a distal end portion defining a distal end, and at least one lumen defined between the proximal end and the distal end, the second elongate tubular member being received within the at least one lumen of the first elongate tubular member, such that the distal end portion of the second elongate tubular member projects from the opening in the distal end portion of the first elongate tubular member; and
 an elongate, shape-imparting element receivable in the at least one lumen of at least one of the first elongate tubular member and the second elongate tubular member, the shape-imparting element imparting a non-rectilinear shape to the distal end portion of at least one of the first elongate tubular member and the second elongate tubular member.

The shape-imparting element may impart a shape to the distal end portions of both of the first and second tubular members. The shape imparted by the shape-imparting element may be a substantially coiled shape. The coiled shape may comprise two coils. A first of the two coils may impart a coiled shape to the distal end portion of the first tubular member to form a first coiled part and a second of the two coils may impart a coiled shape to the distal end portion of the second tubular member to form a second coiled part, the second coiled part being distally spaced from the first coiled part. The first coiled part and the second coiled part may each lie in a plane transverse to a longitudinal axis of the first tubular member and the second tubular member.

In an embodiment, the coiled part of the second tubular member may have a greater circumference than the coiled part of the first tubular member and the shape-imparting element may be of sufficient flexibility so that, in use, the coiled part of the second tubular member is able to be displaced into a position proximally of the coiled part of the first tubular member.

In an embodiment of the catheter assembly, the shape-imparting element may be fast with the second elongate tubular member. The shape-imparting element and the second tubular member may, therefore, be able to be removed from the first tubular member to be replaced by a shape-imparting element and/or a second tubular member of a different configuration.

The catheter assembly may further comprise a second elongate, shape-imparting element to impart a shape to the other of the first and second tubular members.

In an embodiment, the first tubular member and the second tubular member may be axially slidable relative to one another. In another embodiment, the first tubular member and the second tubular member may be fixed with respect to each other.

The catheter assembly may include an introducer extending along at least a part of the length of the tubular members to retain that part of the tubular members in a substantially linear configuration during insertion into an anatomical site or during insertion of the shape-imparting element into the at least one lumen.

The catheter assembly may include a plurality of electrodes, for sensing and/or ablating, on the distal end portion of the first tubular member. Further, the catheter assembly may include a plurality of electrodes, for sensing and/or ablating, on the distal end portion of the second tubular member.

The electrodes of the second tubular member may stand proud of a surface of the second tubular member for improved tissue contact.

The opening in the distal end portion of the first tubular member may be located at the distal end of the first tubular member.

The shape-imparting element may be in the form of a shape memory alloy wire.

The catheter assembly may include a reinforcing element arranged about an outer surface of the first tubular member. The reinforcing element may, for example, be a braided sleeve to provide additional torquability.

Each tubular member may comprise an inner member defining the at least one lumen, a plurality of conductors helically wound about the inner member and a covering of an insulating material overlying the conductors so that the conductors are at least partially embedded in a wall of the tubular member, the conductors of the first tubular member being oppositely wound with respect to the conductors of the second tubular member.

The catheter assembly may include a position-assisting component attached to the distal end of the second tubular member. Further, the catheter assembly may include a tip element via which the position-assisting component is attached to the distal end of the second tubular member. The tip element may be of a malleable material to inhibit trauma to a patient's vascular system. The tip element may be electrically conductive to be able to be used with an impedance-based navigation system.

The position-assisting component may carry a further tubular member that carries at least one electrode. At least a part of the further tubular member may be received over a part of the shape-imparting element with the part of the further tubular member and the distal end part of the second tubular member having a desired, distal, non-linear shape imparted to them by the shape-imparting element.

In a second aspect, there is provided a catheter assembly that comprises:
  a first elongate, tubular member having a proximal end portion defining a proximal end, a distal end portion having an opening therein and defining a distal end, and at least one lumen defined between the proximal end and the distal end, the opening in the distal end portion of the first elongate tubular member being located at the distal end of the first elongate tubular member; and
  a second elongate tubular member having a proximal end portion defining a proximal end, a distal end portion defining a distal end, and at least one lumen defined between the proximal end and the distal end, the second elongate tubular member being received within the first elongate tubular member, such that the distal end portion of the second elongate tubular member projects from the opening in the distal end portion of the first elongate tubular member.

The catheter assembly may include an elongate, shape-imparting element receivable in the at least one lumen of at least one of the first elongate tubular member and the second elongate tubular member, the shape-imparting element imparting a non-linear shape to the distal end portion of at least one of the first elongate tubular member and the second elongate tubular member.

In a third aspect, there is provided a catheter assembly comprising:
  a first elongate tubular member having a proximal end portion defining a proximal end, a distal end portion having an opening therein and defining a distal end, and at least one lumen defined between the proximal end and the distal end;
  a second elongate tubular member having a proximal end portion defining a proximal end, a distal end portion defining a distal end, and at least one lumen defined between the proximal end and the distal end, the second elongate tubular member being received within the at least one lumen of the first elongate tubular member, such that the distal end portion of the second elongate tubular member projects from the opening in the distal end portion of the first elongate tubular member; and
  an elongate, shape-imparting element receivable in the at least one lumen of the second elongate tubular member, the shape-imparting element imparting a non-rectilinear shape to the distal end portions of each of the first elongate tubular member and the second elongate tubular member, the non-rectilinear shapes being axially spaced from each other.

The non-rectilinear shape may be a substantially coiled shape. The coiled shape may comprise two axially spaced coils, each coil lying in a plane substantially transverse to a longitudinal axis of the tubular members.

In a fourth aspect, there is provided a catheter system that comprises:
  a catheter assembly, as described above;
  a handle having a proximal end and a distal end, the catheter assembly extending from the distal end; and
  an operating mechanism carried by the handle for effecting relative displacement between the first tubular member and the second tubular member of the catheter assembly.

The operating mechanism may comprise a first component for effecting coarse adjustment of position of the first tubular member and the second tubular member relative to each other and a second component for effecting finer adjustment of position of the first tubular member and the second tubular member relative to each other.

BRIEF DESCRIPTION OF THE DRAWINGS

FIG. 1 is a schematic, perspective view of an embodiment of a catheter system including a catheter assembly with an introducer of the assembly in a first position;

FIG. 2 is an enlarged, cross-sectional view of the assembly, taken along line 2-2 of FIG. 1 prior to insertion of a shape-imparting element of the assembly;

FIGS. 5 to 7 show various embodiments of a distal end portion of the shape-imparting element;

FIG. 10 shows a schematic, perspective view of yet a further embodiment of a catheter system;

FIG. 11 shows an enlarged, cross-sectional view of the catheter system of FIG. 10 taken along line 11-11 in FIG. 10;

FIG. 12 shows a schematic, perspective view of a distal portion of a variation of the catheter system of FIG. 10;

DETAILED DESCRIPTION OF THE INVENTION

Figures 3, 4:
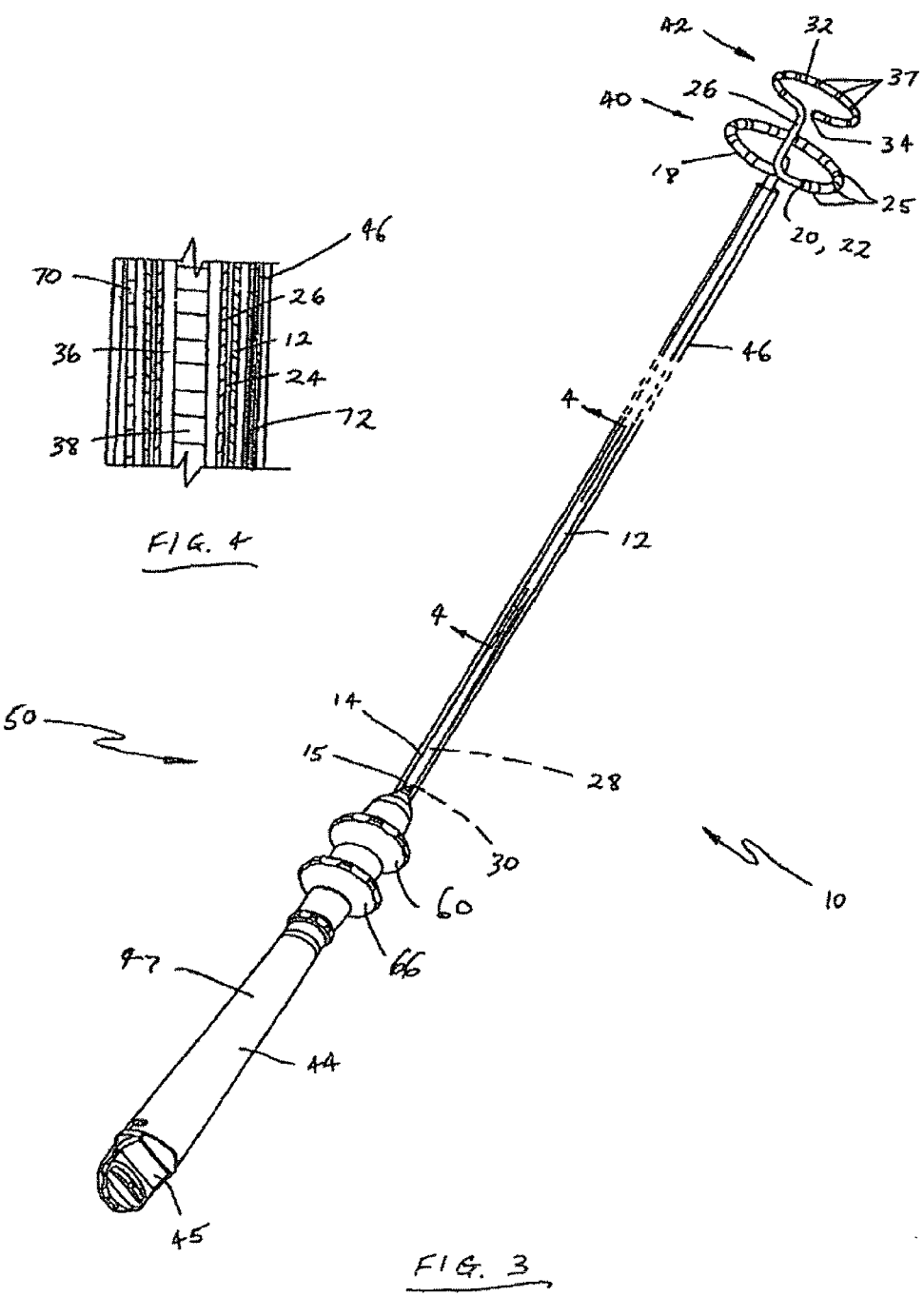
FIG. 3 is a schematic, perspective view of the catheter system of FIG. 1, with the introducer of the catheter assembly in a second position.
FIG. 4 is an enlarged, cross-sectional view of the assembly, taken along line 4-4 of FIG. 3.

In the drawings, reference numeral 10 generally designates an embodiment of a catheter assembly. The catheter assembly 10 includes a first elongate tubular member 12 having a proximal end portion 14 defining a proximal end 15 and a distal end portion 18 defining a distal end 22. An opening 20 is located at the distal end 22 of the first tubular member 12. The tubular member 12 defines a lumen 24 extending between the proximal end 15 and the distal end 22. A plurality of electrodes 25 are provided at spaced intervals on the distal end portion 18 of the first elongate tubular member 12. In this embodiment, the electrodes 25 are used for ablation purposes.

A second elongate tubular member 26 is received in the lumen 24 of the first tubular member 12. In this embodiment, the second tubular member 26 is slidable axially in the lumen 24 of the first tubular member 12. The second tubular member 26 also includes a proximal end portion 28 defining a proximal end 30 and a distal end portion 32 defining a distal end 34. The second tubular member 26 defines a lumen 36 extending between the proximal end 30 and the distal end 34. The distal end 34 of the second elongate tubular member 26 projects from the opening 20 in the distal end portion 18 of the first elongate tubular member 12. A plurality of electrodes 37 are provided at spaced intervals on the distal end portion 32 of the second tubular member 26. In this embodiment, the electrodes 37 are used for sensing or diagnostic purposes.

As described in the Applicant's International Patent Publication No. WO2003/094764 dated May 9, 2003 and entitled "An ablation catheter," the electrodes 37 on the distal end portion 32 of the second tubular member 26 can be used for sensing of electrical activity in walls of pulmonary veins of a patient's vascular system, with the electrodes 25 at the distal end portion 18 of the first tubular member 12 being used for ablation purposes and being arranged, in use, at an ostium of the relevant pulmonary vein.

Each of the first tubular member 12 and the second tubular member 26 is manufactured in accordance with the Applicant's manufacturing techniques, as disclosed in International Patent Publication No. WO 02/32497, entitled "An electrical lead." Briefly, the manufacturing technique comprises providing an inner, tubular member, winding conductors helically about the inner tube and covering the conductors with a jacket of a polymeric material so that the conductors are at least partially embedded in a wall of the tubular lead so formed. Parts of the conductors are exposed by laser cutting the jacket at the desired locations to form access openings to the conductors, the laser cutting operation also removing insulation from the exposed parts of the conductors. The openings are filled with a conductive adhesive and the conductive adhesive, in turn, is coated with a conductive material to form electrodes of the lead. Instead of coating the conductive adhesive, conductive rings of a biocompatible material may be applied over the conductive adhesive to form the electrodes.

The conductive adhesive may be prepared to receive the layers and/or rings, as the case may be, for improving purchase and conductive connection between the conductive adhesive and the overlying layers and/or rings. The conductive adhesive is prepared by roughening the surface of the conductive adhesive, for example, by laser etching, microblasting, or the like.

A benefit of this manufacturing technique is that an unimpeded lumen is provided, with conductors for the electrodes 25, 37 being at least partially embedded in a wall of the respective tubular member 12, 26. Hence, a catheter assembly 10 of relatively small diametrical dimensions can be formed, thereby facilitating navigation of the catheter assembly 10 through the vascular system of a patient's body.

An elongate shape-imparting element 38 is received in the lumen 36 of the second tubular member 26 to impart a non-linear, substantially coiled shape to the distal end portions 18, 32 of both the first tubular member 12 and the second tubular member 26, respectively. The coiled shape comprises two coils, a first coil 40 being associated with the distal end portion 18 of the first tubular member 12 and a second coil 42 being associated with the distal end portion 32 of the second tubular member 26. In this embodiment, the second coil 42 is distally arranged relative to the first coil 40.

Different configurations for the coiled shape of the shape-imparting element 38 are shown in FIGS. 5-7. The different configurations of the shape-imparting element 38 allow the catheter assembly 10 to be tailored to a particular patient's anatomical geometry by selecting the appropriately configured shape-imparting element 38.

The shape-imparting element 38 is formed from a shape memory alloy wire, such as a Nitinol wire, in a superelastic state. A relatively flexible Nitinol tube extends over the Nitinol wire. In the embodiments shown in FIGS. 5 and 7, a shaft 39 of the shape-imparting element 38 is disposed substantially at, or slightly inwardly of, the circumference of the first coil 40. However, in the embodiment shown in FIG. 6, the shaft 39 is disposed substantially on a central axis of the first coil 40. Also, in FIG. 5, the coils 40 and 42 extend from their shafts in opposite directions, while, in FIG. 6, the coils 40 and 42 extend from their shafts in the same direction.

In other embodiments (not shown), separate shape-imparting elements may be provided, one for each of the tubular members 12, 26. In such embodiments, a first shape-imparting element, for imparting a shape to the distal end portion 18 of the first tubular member 12, is inserted into the lumen 24 of the first tubular member 12, and a second shape-imparting element, for imparting a shape to the distal end portion 32 of the second tubular member 26, is inserted into the lumen 36 of the second tubular member 26.

A tubular introducer 46 is received over and extends along the tubular members 12, 26 during insertion of the catheter assembly 10 into an anatomical site to retain the tubular members 12, 26 in a substantially axial or rectilinear configuration. After insertion of the catheter assembly 10 into the anatomical site, the introducer 46 is partially retracted relative to the tubular members 12, 26 to expose their distal end portions 18, 32 and to allow the shape-imparting element 38 to impart its shape to the distal end portions 18, 32 of the tubular members 12, 26, respectively. If it is desired to swap the installed shape-imparting member 38 with another shape-imparting member, the catheter assembly 10 is moved away from the wall of the pulmonary vein, the introducer 46 is extended over the distal end portions of the first tubular member 12 and the second tubular member 26 to straighten the distal end portions, and the shape-imparting element 38 is withdrawn and exchanged with a different shape-imparting element 38. The introducer 46 retains the tubular members 12, 26 in a substantially rectilinear configuration during insertion of the new shape-imparting element 38 into the respective lumen 24, 36.

A catheter system 50 comprises the catheter assembly 10 and a control mechanism, in the form of a handle 44 having a handle body 47, provided at a proximal end of the catheter assembly 10. The shape-imparting element 38, in use, is fast with the handle body 47. An operating mechanism is carried by the handle 44 for effecting relative displacement between the first tubular member 12 and the second tubular member 26. The operating mechanism comprises a first component, in the form of a knob 60 that is axially slidable on the handle body 47. The proximal end of the first tubular member 12 is fast with the knob 60. The second tubular member 26 is fast with either the handle body 47 or the shape-imparting element 38. The shape-imparting element 38 is fast with a locking knob 45, which is removably connectable to a proximal end of the handle 44. Axial movement of the knob 60 effects finer adjustment of position of the first tubular member 12 and the second tubular member 26 relative to each other.

Figure 8:
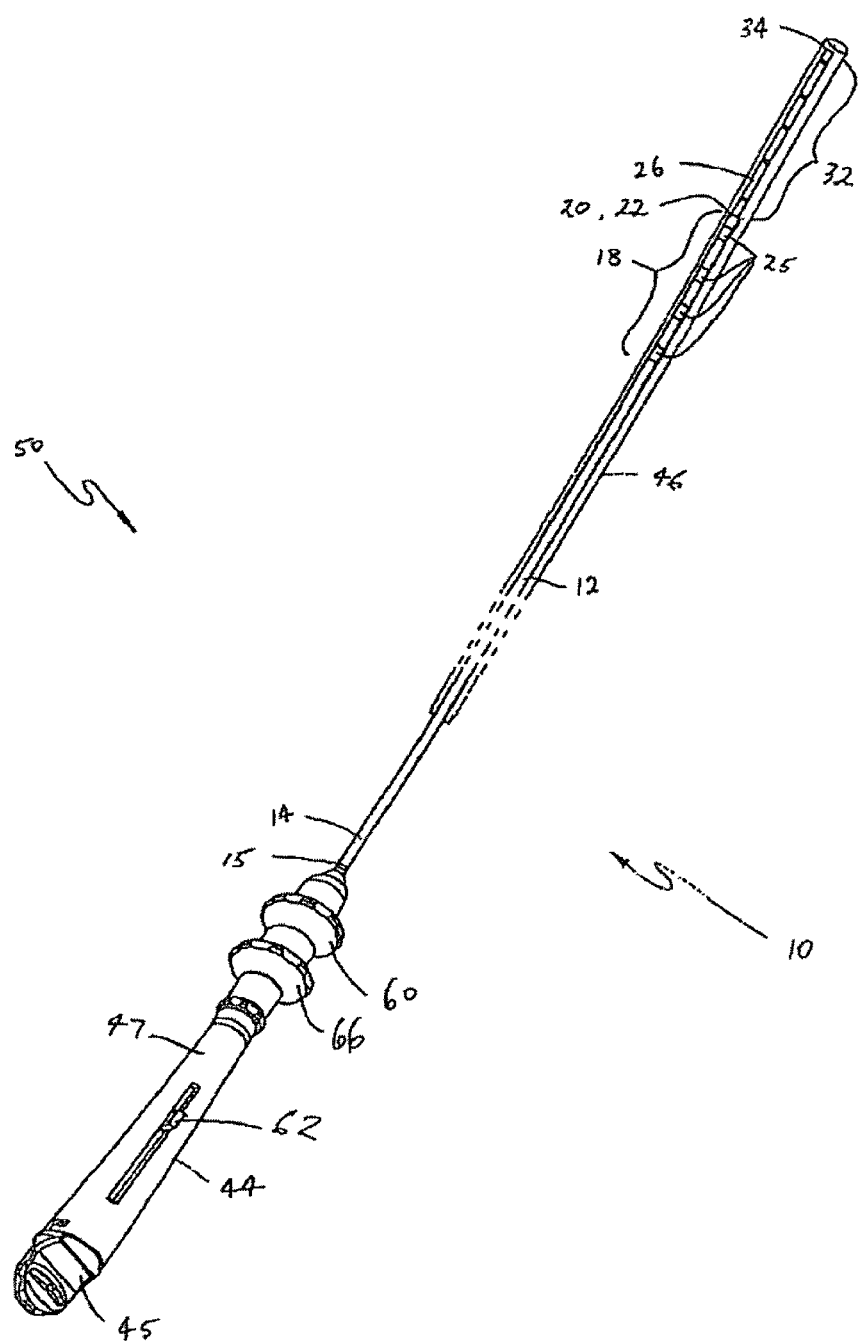
FIG. 8 is a schematic, perspective view of a further embodiment of a catheter system.
Figure 9:
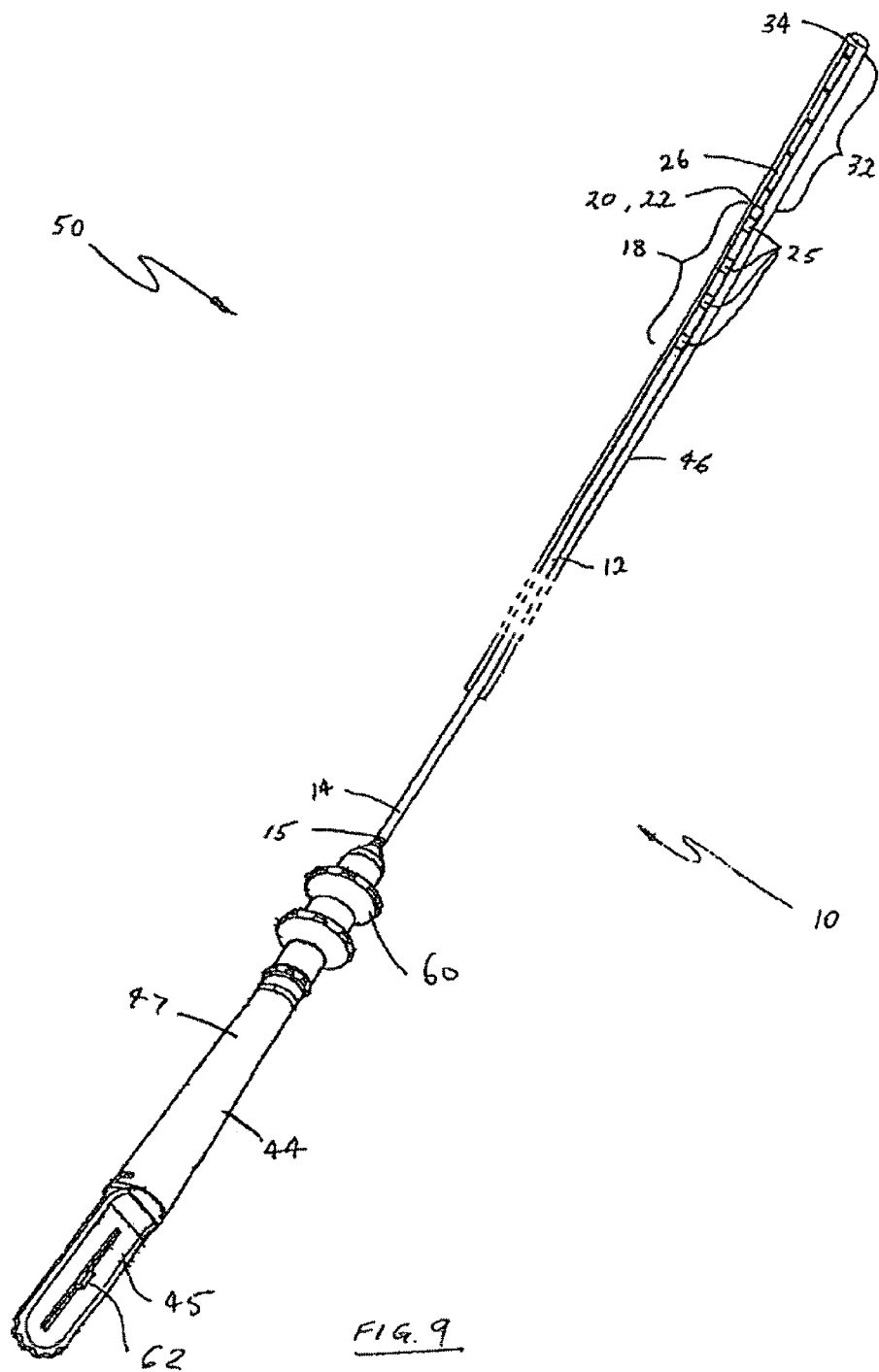
FIG. 9 is a schematic, perspective view of a still further embodiment of a catheter system.

In the embodiments of FIGS. 8 and 9, the operating mechanism carried by the handle 44 also includes a second component, in the form of a slider mechanism 62. The slider mechanism 62 can be provided in the handle body 47, as shown in FIG. 8, or in the locking knob 45, as shown in FIG. 9. In the embodiment shown in FIG. 8, the second tubular member 26 is connected to the slider mechanism 62. In the embodiment shown in FIG. 9, the shape-imparting element 38 (not visible in FIG. 9) is connected to the slider mechanism 62, not to the locking knob 45, and the second tubular member 26 is fast with the shape-imparting element 38.

In the embodiments of both FIGS. 8 and 9, axial movement of the slider mechanism 62 results in corresponding axial movement of the second tubular member 26 relative to the first tubular member 12 for effecting coarse adjustment of position of the first tubular member 12 and the second tubular member 26 relative to each other. The adjustability of the position of the tubular members 12 and 26 relative to each other effects adjustment of the ablating electrodes 25 relative to the sensing electrodes 37. It will also be appreciated that with the coarse and fine adjustment provided by the catheter system 50, a complete circular lesion may be able to be formed about the ostium without the need to rotate the catheter assembly 10.

A steering tube 70 (FIG. 4) is provided for steering the catheter assembly 10 through the patient's vascular system. The steering tube 70 is located between the introducer 46 and the first tubular member 12. The steering tube 70 has a distal end region in which a plurality of slots is provided to enhance bending. A pull wire 72 is carried by the steering tube 70. A distal end of the pull wire 72 is anchored to a distal end of the steering tube 70. A proximal end of the pull wire 72 is attached to a second knob 66, which is axially slidable on the handle 44. Axial movement of the knob 66 towards the proximal end of the catheter assembly 10 effects bending of the distal end of the steering tube 70 to facilitate steering of the catheter assembly 10 through the patient's vascular system.

Referring to FIGS. 10-12, yet a further embodiment of a catheter system 50 is shown. With reference to the previous embodiments, like reference numerals refer to like parts unless otherwise specified.

In this embodiment, a position-assisting component in the form of a push wire 74 is attached to the distal end of the second tubular member 26. The push wire 74 assists in retaining the shape of the coils 40, 42 and also in positioning the distal coil 42 in the pulmonary vein of the patient.

The push wire 74 is received in a tip element 76 as is a distal part 78 of the shape-imparting element 38. The distal part 78 of the shape-imparting element 38 projects through an opening 80 in the distal end of the second tubular member 26 and extends substantially axially. A proximal end of the push wire 74 is attached to a displacement device, such as a slider 79 on the handle body 47 of the handle 44.

The tip element 76 is a molded device of a suitable, malleable plastic material to inhibit causing trauma to the patient's vascular system.

The push wire 74 and the assembly 10 are received in the steering tube 70. As illustrated in FIG. 11, the steering tube 70 includes two pull wires 72 circumferentially spaced 180° from each other.

In a variation (as illustrated in FIG. 12), the push wire 74 carries a further tubular member 82 of a similar construction to the first tubular member 12 and the second tubular member 26. In other words, the further tubular member 82 is also manufactured in accordance with the manufacturing techniques as described above with reference to International Patent Publication No. WO 02/32497.

The further tubular member 82 is received in the tip element 76 and has a hairpin bend 84 formed within the tip element 74. A portion 86 of the tubular member 82 distally of where the hairpin bend 84 is formed is received over the distal part 78 of the shape-imparting element 38 and on to a part of the coil 42 defined by the shape-imparting element 38. The distal end of the second tubular member 26 abuts the distal end of the further tubular member 82 part way along the coil 42 as illustrated at 83. The portion 86 of the tubular member 82 carries an array of electrodes 90, the electrodes 90 being used in conjunction with the electrodes 37 of the second tubular member 26 for sensing or diagnostic purposes. It is, therefore, an advantage of this embodiment, that an increased number of sensing electrodes 37, 90 is provided on the coil 42 improving its ease of use for the clinician. With this configuration, the increased number of electrodes 37, 90 is provided without significantly increasing the diameter of the catheter assembly 10.

If desired, the tip element 76 can be rendered conductive, for example, by being of a conductive polymer, carrying conductive elements or being impregnated with conductive material. The tip element 76 can then be used in conjunction with an impedance-based navigation system to monitor the position of the distal part of the system 50. The need for fluoroscopy, with its attendant radiation risks, may, therefore, be obviated.

Figure 13:
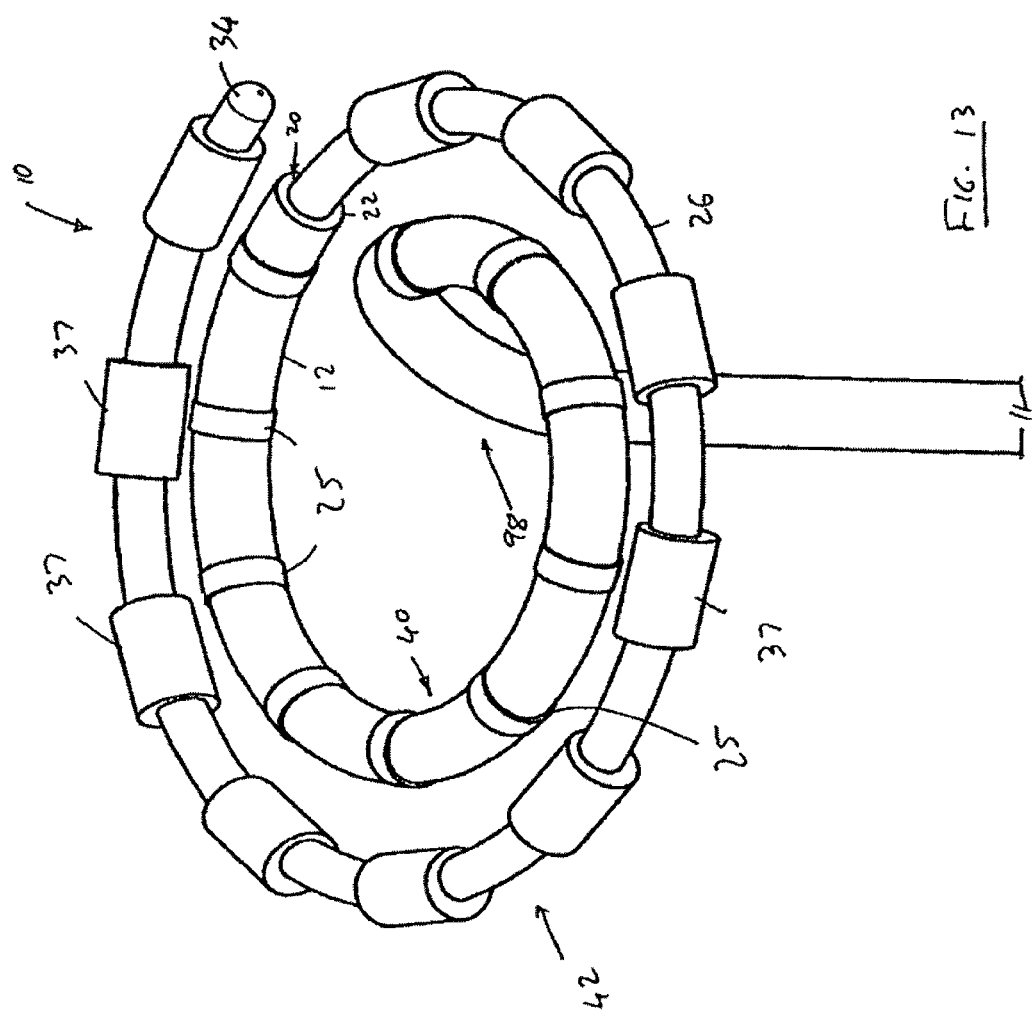
FIG. 13 shows a perspective view of a distal portion of yet another catheter assembly.
Figure 14:
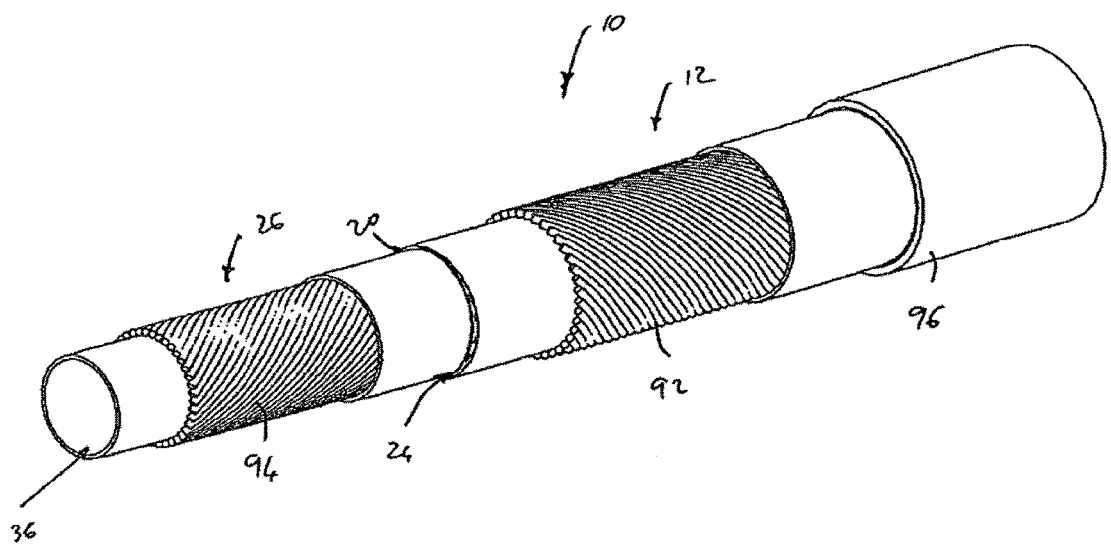
FIG. 14 shows a perspective, stripped away view of the distal part of the catheter assembly of FIG. 13 with the shape-imparting element omitted.
Figure 15:
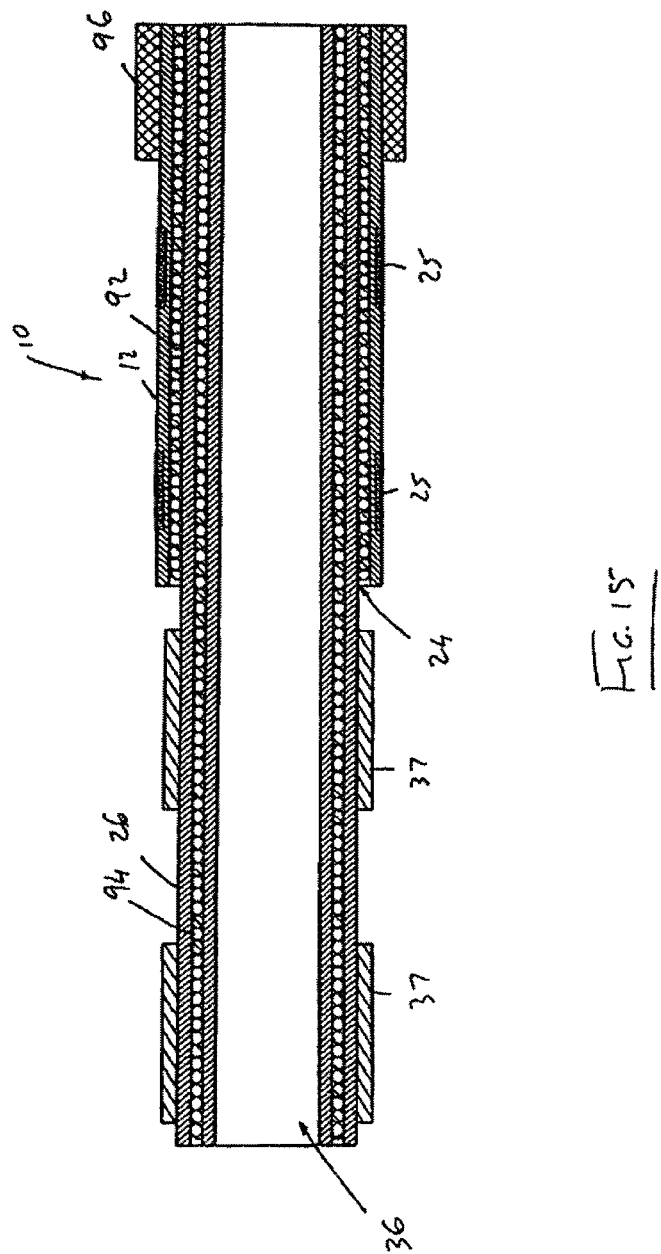
FIG. 15 shows a cross-sectional end view of the distal part of the catheter assembly of FIG. 13 with the shape-imparting element omitted.

In FIGS. 13-15 of the drawings, a still further embodiment of a catheter assembly 10 is illustrated. Once again, with reference to the previously described embodiments, like reference numerals refer to like parts, unless otherwise specified.

As shown most clearly in FIG. 14 of the drawings, conductors 92 of the first tubular member 12 are oppositely wound with respect to conductors 94 of the second tubular member 26. This improves the hoop strength of the catheter assembly 10. It will be appreciated that the opposite winding of the conductors 92 and 94 applies to all the previously described embodiments as well.

The catheter assembly 10 includes a reinforcing element in the form of a braided sleeve 96 arranged about an outer surface of the first tubular member 12 to provide additional torquability to the assembly 10.

Prior to placing the catheter assembly 10 in its operative position at the relevant pulmonary vein, the coils 40 and 42 lie substantially in the same plane. The second coil 42 is larger than the first coil 40. When the catheter assembly 10 is urged distally, the second coil 42 is maintained in position at the ostium and the first coil 40 is received in the pulmonary vein. Thus, the electrodes 37 of the second coil 42 are used for ablation while the electrodes 25 of the first coil 40 are, in use, arranged distally of the electrodes 37 of the second coil 42 and the electrodes 25 are used for sensing.

The two tubular elements 12 and 26 are arranged in a fixed orientation relative to each other and the shaft 39 of the shape-imparting element 38 is kinked to provide a kinked part, as illustrated at 98 in FIG. 13 of the drawings, to the catheter assembly 10 so that the axially extending part of the catheter assembly 10 is arranged inwardly of an imaginary circle circumscribed by the first coil 40. This facilitates insertion of the first loop 40 into the pulmonary vein of the patient's body.

The electrodes 37 stand proud of an outer surface of the second tubular member 26 for improved tissue-electrode contact. For example, the electrodes 37 may be rings of suitable biocompatible material, such as, for example, platinum, which are fixed in position on the tubular member 26.

It will be appreciated that the modular nature of the illustrated catheter assembly 10 facilitates adaptation of the shape configuration of the tubular members 12, 26 while inserted in a patient, as an installed shape-imparting element 38 can be removed and exchanged with a differently configured shape-imparting element 38 without requiring removal of the tubular members 12, 26 from the patient. Also, as the sensing electrodes and ablating electrodes are provided on separate tubular members, adjustment of the relative positions of the sensing and ablating electrodes can be facilitated by relative movement of the tubular members 12, 26. In some embodiments, the second tubular member 26, when fast with the shape-imparting element 38 can be removed from the tubular member 12 and replaced with another tubular member 26 of a different configuration.

It will be appreciated by persons skilled in the art that numerous variations and/or modifications may be made to the described embodiments without departing from the broadly described scope. The present embodiments are, therefore, to be considered in all respects as illustrative and not restrictive. For example, other embodiments (not shown) can include the following variations or modifications:

the opening in the distal end portion of the first tubular member 12 may be set back from the distal end 22, such that the second tubular member 26 extends through a sidewall of the first tubular member 12;

a distal end of the shape-imparting element 38 may be fast with the distal end 34 of the second elongate tubular member 26, such that insertion of the second tubular member 26 into the first tubular member 12 imparts the non-linear shape to the exposed distal end portion 18 of the first tubular member 12. In this embodiment, a sub-assembly comprising the shape-imparting element 38 and the tubular member 26 can be removed from the lumen 24 of the first tubular member 12 and replaced by a different sub-assembly having a different sensing electrode configuration and/or a different arrangement of coils 40, 42;

the introducer 46 can take the form of an elongate guide rod for insertion in the second tubular member 26;

two different shape-imparting elements may be used to form the coils 40 and 42. The shape-imparting elements may both be received in the lumen 36 of the second tubular member 26 or, instead, one may be received in the lumen 24 of the first tubular member 12 and the other may be received in the lumen 36 of the second tubular member 26.

What is claimed is:

1. A catheter assembly comprising:

a first elongate tubular member having a proximal end portion defining a proximal end, a distal end portion carrying at least one electrode thereon and having an opening therein and defining a distal end of the first elongate tubular member, and at least one lumen defined between the proximal end and the distal end;

a second elongate tubular member having a proximal end portion defining a proximal end, a distal end portion carrying at least another electrode thereon and defining a distal end, and at least one lumen defined between the proximal end and the distal end of the second elongate tubular member, the second elongate tubular member being received within the at least one lumen of the first elongate tubular member, such that the distal end portion of the second elongate tubular member carrying the at least another electrode thereon projects from the opening in the distal end portion of the first elongate tubular member; and an elongate, shape-imparting element receivable in the at least one lumen of the second elongate tubular member, in which the shape-imparting element is axially displaceable relative to the distal end of the first elongate tubular member and the second elongate tubular member, the shape-imparting element imparting a first non-rectilinear shape to the distal end portion of at least one of the first elongate tubular member and the second elongate tubular member, wherein the shape-imparting element imparts a second non-rectilinear shape to the distal end portions of both of the first and the second tubular members.

2. The catheter assembly of claim 1, wherein:
the first non-rectilinear shape and the second non-rectilinear shape are axially spaced from each other.

3. The catheter assembly of claim 2, wherein at least one of the first non-rectilinear shape and the second non-rectilinear shape is a substantially coiled shape.

4. The catheter assembly of claim 3, wherein the coiled shape comprises two axially spaced coils, each coil lying in a plane substantially transverse to a longitudinal axis of the first elongate tubular member and the second elongate tubular member.

5. The catheter assembly of claim 1, wherein the shape-imparting element comprises a wire formed at least in part from a shape memory alloy.

6. The catheter assembly of claim 1, further comprising a reinforcing element arranged about an outer surface of the first tubular member.

7. The catheter assembly of claim 6, wherein the reinforcing element comprises a braided sleeve.

8. The catheter assembly of claim 1, wherein each of the first tubular member and the second tubular member comprises an inner member defining the at least one lumen thereof.

9. The catheter assembly of claim 8, further comprising conductors helically wound about the inner member of each of the first tubular member and the second tubular member.

10. The catheter assembly of claim 9, further comprising an insulating material overlaid on the conductors wound about the inner member of each of the first tubular member and the second tubular member such that the conductors of each of the first tubular member and the second tubular member are at least partially embedded in a wall of the respective tubular member.

11. The catheter assembly of claim 9, wherein the conductors of the first tubular member are oppositely wound with respect to the conductors of the second tubular member.

12. The catheter assembly of claim 2, wherein the shape-imparting element comprises a wire formed at least in part from a shape memory alloy.

13. The catheter assembly of claim 2, further comprising a reinforcing element arranged about an outer surface of the first tubular member.

14. The catheter assembly of claim 13, wherein the reinforcing element comprises a braided sleeve.

15. The catheter assembly of claim 2, wherein each of the first tubular member and the second tubular member comprises an inner member defining the at least one lumen thereof.

16. The catheter assembly of claim 15, further comprising conductors helically wound about the inner member of each of the first tubular member and the second tubular member.

17. The catheter assembly of claim 16, further comprising an insulating material overlaid on the conductors wound about the inner member of each of the first tubular member and the second tubular member such that the conductors of each of the first tubular member and the second tubular member are at least partially embedded in a wall of the respective tubular member.

18. The catheter assembly of claim 16, wherein the conductors of the first tubular member are oppositely wound with respect to the conductors of the second tubular member.

19. The catheter assembly of claim 1, wherein the shape-imparting element comprises a push wire.

\* \* \* \* \*